(12) United States Patent
Bergmann et al.

(10) Patent No.: US 7,547,553 B2
(45) Date of Patent: Jun. 16, 2009

(54) IN VITRO METHOD FOR THE DIAGNOSIS OF NEURODEGENERATIVE DISEASES

(75) Inventors: Andreas Bergmann, Berlin (DE); Andrea Ernst, Hennigsdorf (DE); Harald Hampel, München (DE)

(73) Assignee: B.R.A.H.M.S. Aktiengesellschaft, Hennigsdorf (DE)

( * ) Notice: Subject to any disclaimer, the term of this patent is extended or adjusted under 35 U.S.C. 154(b) by 1 day.

(21) Appl. No.: 11/997,250

(22) PCT Filed: Jul. 24, 2006

(86) PCT No.: PCT/EP2006/007272

§ 371 (c)(1), (2), (4) Date: Jan. 29, 2008

(87) PCT Pub. No.: WO2007/014667

PCT Pub. Date: Feb. 8, 2007

(65) Prior Publication Data

US 2008/0199966 A1    Aug. 21, 2008

(30) Foreign Application Priority Data

Aug. 1, 2005    (DE) ................. 10 2005 036 094

(51) Int. Cl.
*G01N 33/68*    (2006.01)
*G01N 33/00*    (2006.01)
*G01N 33/566*   (2006.01)
*G01N 33/543*   (2006.01)
*G01N 33/536*   (2006.01)
*G01N 33/53*    (2006.01)

(52) U.S. Cl. .................. 436/86; 436/501; 436/518; 436/536; 436/811; 436/815

(58) Field of Classification Search .................. 436/86, 436/501, 518, 536, 811, 815
See application file for complete search history.

(56) References Cited

FOREIGN PATENT DOCUMENTS

WO    2004/090546    10/2004

OTHER PUBLICATIONS

International Preliminary Report on Patentability for PCT/EP2006/007272.
Frank et al., "Biological markers for therapeutic trials in Alzheimer's disease—Proceedings of the biological markers working group; NIA initiative on neuroimaging in Alzheimer's disease", Neurobiology of Aging 24 (2003) 521-536.
Teunissen et al., "Biochemical markers related to Alzheimer's dementia in serum and cerebrospinal fluid", Neurobiology of Aging 23 (2002) 485-508.

(Continued)

*Primary Examiner*—Maureen M Wallenhorst
*Assistant Examiner*—Keri A Moss
(74) *Attorney, Agent, or Firm*—Heslin Rothenberg Farley & Mesiti P.C.

(57) ABSTRACT

An in vitro method for the detection, determination of severity and monitoring and prognosis of neurodegenerative diseases is disclosed. The presence and/or concentration of the physiologically inactive proadrenomedullin (proADM) partial peptide, in particular, the midregional proADM partial peptide, is determined in a biological fluid of a patient who is suffering from a neurodegenerative disease or is suspected of having such a disease. Conclusions about the presence, course, severity or success of a treatment of the neurodegenerative disease are drawn on the basis of the presence and/or concentration of the specific partial peptide in the biological sample.

12 Claims, 1 Drawing Sheet

OTHER PUBLICATIONS

Figure 1:
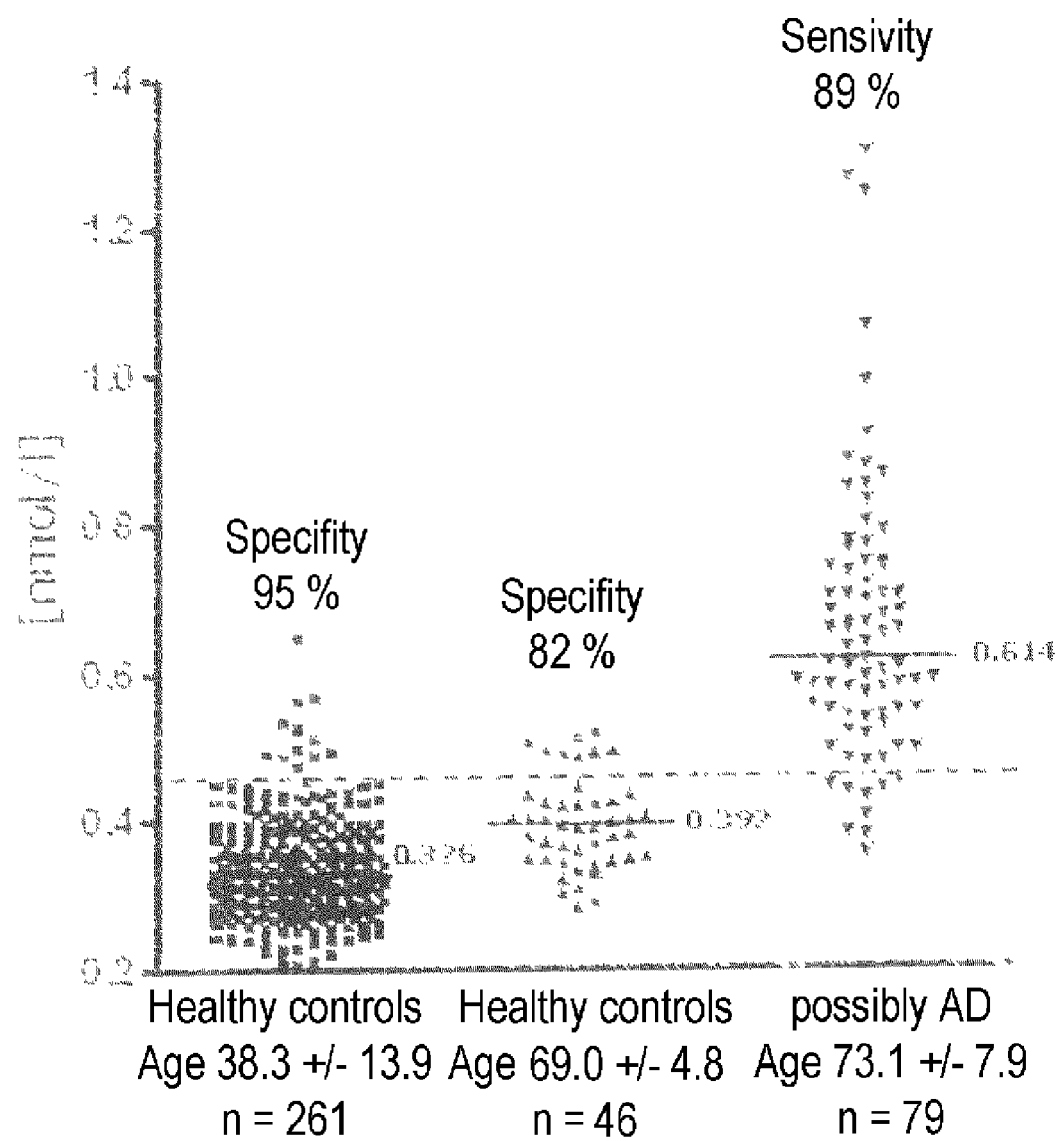

Beinfeld et al., "Prohormone and proneuropeptide processing", Endocrine vol. 8(1), Feb. 1998, 1-5.

Beltowski et al., "Adrenomedullin—What do we know 10 years since its Discovery?" Polish Journal of Pharmacology, 2004, vol. 56, 5-27.

Bunton et al., "The clinical relevance of adrenomedullin: a promising profile?", Pharmacology & Therapeutics 103 (2004), 179-201.

Chu et al., "Studies of the microvascular effects of adrenomedullin and related peptides", Peptides 22 (2001) 1881-1886.

Elsasser et al., "Adrenomedullin Binding Protein in the Plasma of Multiple Species: Characterization by Radioligand Blotting", Endocrinology, vol. 140(10), 4908-4911.

Tanenao ETO, "A review of the biological properties and clinical implications of adrenomedullin and proadrenomedullin N-terminal 20 peptide (PAMP), hypotensive and vasodilating peptides", Peptides 22 (2001), 1693-1711.

David S. Geldmacher, MD., "Dementia with Lewy bodies: Diagnosis and clinical approach", Cleveland Clinic Journal of Medicine, vol. 71(10), Oct. 2004, 789-800.

Growdon et al., Consensus Report of the Working Group on: "Molecular and Biochemical Markers of Alzheimer's Disease", [The Ronald and Nancy Reagan Research Institute of the Alzheimer's Association and the National Institute on Aging Working Group], Neurobiology of Aging, vol. 19(2), 1998, 109-116.

Ichiki et al., "Distribution and characterization of immunoreactive adrenomedullin in human tissue and plasma", FEBS Letters, 338 (1994), 6-10.

Kis et al., "Adrenomedullin in the cerebral circulation", Peptides 22, (2001) 1825-1834.

Kitamura et al., Identification and hypotensive activity of proadrenomedullin N-terminal 20 peptide (PAMP), FEBS Letters 351 (1994), 35-37.

Kitamura et al., "Adrenomedullin and PAMP: Discovery, Structures, and Cardiovascular Functions", Microscopy Research and Technique, vol. 57 (2002), 3-13.

Meeran et al., "Circulating Adrenomedullin Does Not Regulate Systemic Blood Pressure but Increases Plasma Prolactin after Intravenous Infusion in Humans: A Pharmacokinetic Study", Journal of Clinical Endocrinology and Metabolism, vol. 82(1), 95-100.

Morgenthaler et al., "Measurement of mid regional proadrenomedullin (MR-proADM) in plasma with an immunoluminometric assay", Clinical Chemistry, 2005, 1-25.

Nicholls et al., "Bioactivity of adrenomedullin and proadrenomedullin N-terminal 20 peptide in man", Peptides 22 (2001), 1745-1752.

Satoh et al., "Adrenomedullin in Human Brain, Adrenal Glands and Tumor Tissues of Pheochromocytoma, Ganglioneuroblastoma and Neuroblastoma", Journal of Clinical Endocrinology and Metabolism, vol. 80(5), 1750-1752.

Dennis J. Selkoe, "Alzheimer's Disease: Genes, Proteins, and Therapy", Physiological Reviews vol. 81: 741-766.

Stroud et al., "Signal sequence recognition and protein targeting", Current Opinion Structure Biology, 9, 754-9.

Struck et al., "Identification of an Adrenomedullin precursor fragment in plasma of sepsis patients", Peptides 25 (2004), 1369-1372.

Sugo et al., "Endothelial Cells Actively Synthesize and Secrete Adrenomedullin", Biochemical and Biophysical Research Communications, vol. 201(3), Jun. 1994, 1160-1166.

Elisabeth Tarkowski, "Cytokines in Dementias", Current Drug Targets—Inflammation & Allergy, 2002, vol. 1(2), 193-200.

Tarkowski et al., "Cerebral pattern of pro-and anti-inflammatory cytokines in dementias", Brain Research Bulletin 61 (2003), 255-260.

Taylor et al., "Adrenomedullin and central cardiovascular regulation", Peptides 22 (2001) 1803-1807.

Teunissen et al., "Biochemical markers related to Alzheimer's dementia in serum and cerebrospinal fluid", Neurobiology of Aging 23 (2002) 485-508.

I.G. McKeith, "Dementia with lewy bodies", British Hournal of Psychiatry 180 (2002), 144-147.

IN VITRO METHOD FOR THE DIAGNOSIS OF NEURODEGENERATIVE DISEASES

CROSS REFERENCE TO RELATED APPLICATIONS

This application is a 371 filing of PCT International application no. PCT/EP2006/007272 filed Jul. 24, 2006 and published in German as WO 2007/014667 on Feb. 8, 2007 which claims the priority of German application no. 10 2005 036 094.7 filed Aug. 1, 2005. The disclosures of these applications and all other patents, published applications and other references cited herein are hereby incorporated by reference in their entirety.

The present invention relates to a novel in vitro method for the diagnosis of neurodegenerative diseases, in particular of dementia, such as Alzheimer's disease.

In the context of the present invention, the term "diagnosis" is used as a general term for medical determinations which, depending on the clinical state of the patient for whom the determination is carried out, may be based on different problems and which serve in particular for detection and early detection, determination of severity and monitoring, including monitoring during the treatment, and prognosis of the future course of the disease. What is of particular importance in the present context is that a diagnosis can also be a negative diagnosis in which the presence of a certain disease is reliably excluded on the basis of the failure to find a certain feature typical of the disease, for example the non-detectability of a biomarker associated with a relevant disease in a blood sample of a patient.

Also of considerable value for the negative diagnosis are biomarkers which can be found in elevated concentration in a plurality of different diseases and therefore do not alone by themselves permit a positive diagnosis of a specific disease—although as a rule they can also be decisive for the positive diagnosis with the use of further clinical or biochemical parameters.

The diseases with the diagnosis of which the present invention is concerned tend to be slowly developing, chronic neurodegenerative diseases of non-infectious aetiology, in particular presenile dementias.

Dementias are generally defined as diseases for which a common feature is the loss of acquired intellectual capabilities, especially of the memory, and of the normal level of the personality as a consequence of brain damage. Dementias are as a rule relatively slowly developing diseases of chronic character. If dementia phenomena occur before old age, in middle aged people, they are referred to as presenile dementias and, on the basis of the symptoms typical of them and pathological changes in the brain, a differentiation is made in particular between the following diseases or groups of diseases:

Alzheimer's dementia (AD) (Alzheimer's disease) is the most frequent neurodegenerative dementia and accounts for ⅔ of all cases of dementia. AD is distinguished by three important pathological features which, however, can only be detected with certainty post-mortem: the formation of amyloid plaques and neurofibrillar bundles and the loss of nerve cells (for an overview, cf. 19; references in the description in the form of numbers refer to the list of references following the description). Amyloid plaques consist of extraneuronal aggregates of amyloid-β-protein, while the neurofibril bundles contain mainly tau-protein and neurofilaments. It is presumed that the plaque and neurofibril formation is the cause of the death of nerve cells.

The most important symptoms of AD are increasing dysfunctions of memory and intellect with relatively persistent emotional responsiveness, these symptoms being accompanied by further less specific disturbances which make it difficult to differentiate AD from other forms of dementia.

Dementia with Lewy bodies (DLB) is the second most frequent cause of a dementia after Alzheimer's dementia. Neuropathologically, DLB is characterized by the occurrence of so-called Lewy bodies in the brain stem and in the cortex. These Lewy bodies consist predominantly of aggregates of the presynaptic protein (α-synuclein) and ubiquitin. Lewy body pathology can be associated to different extents with neuropathological changes typical of Alzheimer's and Parkinson's disease. Thus, in DLB too, the formation of beta-amyloid and senile plaques occurs, but not neurofibril bundles (for an overview, cf. 14). Lewy bodies are also present in the brain of patients with Parkinson's disease, even if in a different distribution.

Key symptoms of DLB are a progressive cognitive disturbance, episodes of confusion with fluctuating attention and consciousness, Parkinsonism, frequent falls and syncopes (brief, paroxysmal unconsciousness). The sensitivity and specificity of the diagnostic criteria show high specificity throughout but a very low sensitivity in some cases. This means that DLB is frequently not diagnosed in clinical routine.

Frontotemporal dementia (FTD) is also referred to as Pick's disease and accounts for about 20% of presenile dementias. FTD is genetic in some cases and is among the so-called tauopathies, which are distinguished by overexpression or underexpression of a tau-protein subtype or by the expression of a mutated tau-protein. Neuropathological symptoms are local atrophy of the frontal and/or temporal cortex and of the substantia nigra and of the basal ganglia. This results in different levels of speech disturbance, a change of personality and behavioural peculiarities. Overall, FTD is underdiagnosed with a sensitivity of 93% and a specificity of only 23%, AD being the most frequent misdiagnosis.

The term vascular dementia (VAD) covers diseases in which a dementia is triggered owing to disturbed blood flow in the brain. There are different types of VAD, of which multi-infarction dementia (MID) and subcortical VAD (also referred to as Binswanger's disease) are the most frequent forms.

Binswanger's disease is a slowly progressing dementia which is characterized pathologically by cerebrovascular legions in the white brain substance. Clinically this results in behavioural peculiarities, such as agitation, irritability, depression and euphoria, and slight memory disturbance.

Multi-infarction dementia arises gradually as a consequence of several small strokes, also referred to as transient ischaemic attacks (TIA), which led to the destruction of brain tissue in the cortex and/or subcortical areas. The strokes may also have remained completely unnoticed, in which case the dementia is the first noticeable consequence. In the presence of MID, there is a gradual decrease in cognitive capabilities, associated with severe depressions, mood fluctuations and epilepsy.

A diagnosis of dementias is performed nowadays predominantly on the basis of neuropsychological investigations and the observation of the development of the disease and its course using exclusion criteria for certain forms of dementia. In very many cases, these investigations give ambiguous results, which explain the abovementioned numbers for the underdiagnosed forms of dementia or incorrectly diagnosed cases. The cerebral changes typical of the disease cannot of course be established directly in living patients and technical medical investigations of brain function by means of, for example, X-ray tomography or MRI are complicated and expensive.

For the diagnosis of Alzheimer's disease, the Ronald and Nancy Reagan Institute of the Alzheimer's Association and the NIA Working Group published guidelines for the criteria which are set for an ideal biomarker for the detection of AD (7). The following criteria should ideally be fulfilled by the biomarker:

1. It should be brain-specific and detect a fundamental feature of the neuropathology of these diseases.

2. The diagnostic sensitivity and the specificity should be at least 80%.

3. The disease-specific change of the biomarker should manifest itself in as earlier a stage of the disease as possible, in order to be able to begin suitable therapeutic measures (9).

There has to date, however, been no biomarker which could be used in clinical routine in the blood or the cerebrospinal fluid with sufficient certainty for the early and differential diagnosis of AD and which fulfils all abovementioned criteria. At present, various potential marker candidates are being investigated, including inflammation markers, such as IL-6 and TNFα, markers for oxidative stress, such as 3-nitrotyrosine, and markers which are associated with characteristic pathological changes of the AD, such as amyloid β, which is a main constituent of the amyloid plaques, and the tau-protein, which is a substantial constituent of the neurofibril bundles (cf. the overview in 7; 26).

There is a current need for supplementary methods for investigation which give valid laboratory findings, are based on a determination of substances in blood or plasma samples which are suitable as biomarkers for dementias, in particular for Alzheimer's dementia (AD), and are suitable for a positive diagnosis and/or for a negative exclusion diagnosis in patients in whom the presence of a dementia, in particular of AD, are suspected.

The present invention provides such a method of investigation in the form of an in vitro method for the detection, for the determination of severity and for the monitoring and prognosis of neurodegenerative diseases, in which the presence and/or concentration of a physiologically inactive proadrenomedullin partial peptide is determined in a biological fluid of a patient who is suffering from a neurodegenerative disease or is suspected of suffering from such a disease, and conclusions about the presence, the course, the severity or the success of a treatment of the neurodegenerative disease are drawn on the basis of the presence and/or concentration found or of the absence of the specific partial peptide.

Advantageous or preferred developments of a method according to Claim 1 are described in subclaims 2 to 10.

The present invention is based on considerations by the inventors for improving the diagnosis of dementias by applying the discovery that the known forms of presenile dementia explained in more detail at the outset are also accompanied— to different extents—by inflammatory processes and endothelial damage, which are regarded as essential for the development, the symptoms and the course of dementias, which is why neurodegenerative diseases can also be regarded as neuroinflammatory diseases.

Thus, Alzheimer's disease is characterized, inter alia, by the occurrence of chronic local inflammatory reactions in the brain with participation of various inflammatory proteins, such as complement factors, acute-phase proteins and proinflammatory cytokines (26).

Inflammatory processes also play a role in the origin of vascular dementias (VAD). The levels of TNFα, TGFβ, IL-6 and GM-CSF (granulocyte-macrophage colony-stimulating factor) are substantially elevated in patients with VAD (23, 24).

In DLB, too, inflammatory processes appear to play a role. Thus, the number of activated microglia cells in the brain of patients with DLB is increased, and proinflammatory cytokines, such as TNFα, are overexpressed in certain regions of the brain, such as the amygdala and the hippocampus.

On the other hand, there are only isolated indications of the occurrence of inflammatory reactions in the brain of FTD patients.

Starting (i) from the hypothesis that the neuroinflammatory processes associated with dementia lead to blood flow disturbances, in particular also to microcirculatory disturbances of the brain, and (ii) that to this extent there is a similarity with cardiovascular diseases which are associated with blood flow disturbances or disturbances of the microcirculation (4) of the cardiac tissue, and (iii) from analytical findings which show that increased formation of, inter alia, the strong vasodilator adrenomedullin is detectable in such cardiovascular diseases, and finally (iv) utilizing the possibility of determining the formation or physiological release of adrenomedullin reliably and in clinically valid form with the aid of a novel immunoassay of the Applicant which measures the concentration of a midregional, physiologically inactive preproadrenomedullin partial peptide (MR-proADM; SEQ ID NO: 2), the inventors examined the question as to whether it is possible to detect increased concentrations of the abovementioned midregional proadrenomedullin partial peptide (MR-proADM) in plasma also in the case of patients with dementias, in particular patients in whom Alzheimer's dementia (AD) had been diagnosed with high probability and who otherwise suffered from no known disease associated with increased adrenomedullin production.

The measured results in EDTA plasma samples of apparently healthy normal persons and Alzheimer patients, described below in the experimental section, gave a clear, diagnostically significant correlation between the concentrations found for the midregional proadrenomedullin partial peptide (MR-proADM; SEQ ID NO: 2) and the presence of dementia symptoms which had led to the diagnosis of "probable Alzheimer's disease".

Although the investigations have been limited to date to plasma samples of Alzheimer patients, the inventors assume that—possibly with different typical concentration ranges— characteristic increases of the MR-proADM concentrations in patient plasmas would have to be detectable also in the case of other neuroinflammatory dementia forms, in particular in vascular dementia (VAD) and dementia with lewy bodies (DLB). This assumption is also supported in particular by more recent measurements by the applicant of the concentrations of the biomarker procalcitonin in cerebrospinal fluid (CSF), which demonstrates an immunodiagnostically recognizable relationship of said diseases (cf. patent application DE 10 2005 034 174.8 of 21 Aug. 2005).

The assay method used for the measurements described in the experimental section for MR-proADM concentrations in patient plasmas is based on a non-competitive immunoluminometric sandwich assay, which is described in more detail in WO 2004/090546 A1 (or EP 1 488 209 A1) of the Applicant, in particular in paragraphs 5 and 6 of the experimental section, and in (21). The general statements on the problem of adrenomedullin determination in patient samples and the explanations for carrying out the assay in WO 2004/090546 A1 and in (21) are hereby incorporated by reference for supplementing the statements in the present Application.

Adrenomedullin (ADM) is a peptide hormone which consists of 52 amino acids and is formed in its biosynthesis from a longer precursor peptide comprising 185 amino acids (SEQ ID NO: 1). The biosynthesis of adrenomedullin, as in the case of other peptide hormones, takes place initially as a prepro-hormone on membrane (Golgi)-bound ribosomes. After elimination of the hydrophobic N-terminal signal sequence consisting of 21 amino acids by signal peptidases and folding of the remaining propeptides in the lumen of the endoplasmic reticulum, the propeptides in the Golgi apparatus are packed in vesicles and transported to the cell membrane (20). During the transport, processing of the propeptides to mature hormones is effected by prohormone convertases on generally dibasic amino acid sequences (1). Via various stimuli, the physiologically active, mature peptides (peptide hormones) are then released into the extracellular space or into the plasma. After release, the mature active peptides are usually rapidly deactivated by proteolysis and/or removed from the circulation by binding to their receptors. They therefore generally have only short physiological half-lives. Thus, a half-life of only 22 minutes in the plasma was determined for ADM (15).

Adrenomedullin is expressed in high concentrations by vascular endothelial cells (22) in the adrenal medulla, in the pancreas, in the atrium, in the lungs, in the small intestine (10) and in the brain (18). ADM has a variety of biological activities (a more recent overview is to be found in 2). Thus, ADM leads to a reduction in blood pressure, to greater sodium excretion and to an increase in renal blood flow. ADM also inhibits the secretion of ACTH (adrenocorticotropic hormone) by the pituitary gland and HCl secretion by the gastrointestinal mucosa. Furthermore, ADM has antimicrobial properties against gram-positive and gram-negative bacteria.

The preproadrenomedullin precursor of ADM (SEQ ID NO: 1) contains, in addition to ADM itself, further segments or partial peptides, which include a further active peptide, the proadrenomedullin N-terminal 20 peptide (PAMP), which likewise has hypotensive, i.e. blood pressure-reducing, properties (12). A C-terminal partial peptide which has been investigated in less detail, is referred to as adrenotensin and comprises 33 amino acids (amino acids 153-185 of preproADM; cf. for example description in 21) is likewise vasoactive according to the findings to date (a vasoconstrictor).

The possibility of the analytical determination of ADM itself is adversely affected by its short half-life, by its autocrine or paracrine action and also by the masking of the hormone by an ADM-binding protein (5) and its extreme physical properties (adhesion to surfaces of vessels). A reliable, reproducible direct quantification of ADM in the blood of patients which is suitable for routine purposes is therefore not possible.

A breakthrough for the reliable determination of the formation or release of ADM by measurement of a blood or plasma biomarker was made only through the finding that a stable pro-ADM fragment, the abovementioned preproADM 45-92 or MR-proADM (SEQ ID NO: 2; cf. also WO 2004/090546 A1 or 21) is also present in the blood and is formed in a stoichiometric ratio to the most important of the active pro-ADM peptides ADM and PAMP, but is inactive and stable, so that its quantification by means of an immunoassay in a valid, reproducible form was possible.

The results of a significant increase in the measurable plasma concentration of MR-proADM in Alzheimer patients, reported in the present Application, can be interpreted as confirmation of the working hypothesis that increased ADM production, measurable as increased MR-proADM plasma concentration, is to be observed generally in the case of pathological endothelial damage or damage to the microcirculation. Dementias constitute an impairment of the microcirculation in the brain, while the heart tissue is affected in the case of cardiovascular diseases.

The significant increases in the measurable MR-proADM plasma concentrations found on the basis of a relatively small group of 20 patients with cardiovascular diseases (heart failure) and shown in WO 2004/090546 has in the meantime been completely confirmed in more extensive investigations with a larger group of 232 patients with chronic heart failure (CHF; also digestive heart failure). Thus, measurable MR-proADM concentrations of the patients, detected by a sandwich assay according to WO 2004/090546 with a functional assay sensitivity (interassay CV<20%) of 0.12 nmol/l, could be clearly correlated with the severity of the respective heart failure. While the mean value for the plasma concentrations of MR-proADM in healthy control persons (264 persons) was determined as 0.33±0.07 nmol/l (value range from 0.10 to 0.64 nmol/l), the mean value for the patients suffering from digestive heart failure was 0.8±0.55 nmol/l and increased with the severity of the disease (classified according to the NVHA classification as classes I, II, III and IV; mean MR-proADM concentrations in nmol/l for class I 0.41±0.15; class II 0.61±0.31; class III 0.77±0.44; class IV 1.35±0.77). An increase in the MR-proADM value also proved to be a powerful prognosis marker for the expectation of survival of a patient suffering from heart failure (an increase in the MR-proADM value proved to be a prognosis marker for poor chances of survival with a hazard ratio of 1.181 per 0.1 nmol/l, p<0.0001).

The invention is explained in more detail below with reference to measured results and a figure.

FIG. 1 shows the results of the measurement of the MR-proADM concentrations in EDTA plasmas of healthy control persons, the evaluation having been carried out on the basis of two age groups, and of patients diagnosed with "probable Alzheimer's dementia".

EXPERIMENTAL SECTION

Description of Assay

The measurement of the mid-regional proADM 45-92 (MR-proADM; SEQ ID NO: 2) in the plasma was effected by means of an immunoluminometric sandwich assay substantially as described in the experimental section of WO 2004/090546 or the corresponding EP 1 488 209 A1 or in (21) or (16).

In particular 10 μl of sample/calibrator and 200 μl of tracer (marked first antibody) were introduced into the tubes coated with the second antibody and incubated for 2 hours at room temperature (18-24° C.) with mixing (170-300 rpm). Thereafter the liquid phase was decanted and the tubes were washed four times with 1 ml of LUMItest wash solution (B.R.A.H.M.S Aktiengesellschaft, Hennigsdorf, Germany). The bound chemiluminescence was then measured for 1 s per tube using an LB952T luminometer (Berthold, Wildbad, Germany).

In control measurements, it was found that MR-proADM should be measured in EDTA plasmas since substantially lower values are obtained in serum than in EDTA plasma, and heparin plasma and citrate plasma also give deviating values which would necessitate another calibration.

Measurement of MR-proADM in the Plasma of Healthy Controls and Patients Suffering from a Probable Alzheimer's Dementia For determining a reference value for the concentration of the MR-proADM, a measurement was carried out in EDTA plasmas of 264 healthy control persons who suffered neither from a neurodegenerative disease nor from any other recognizable disease (cardiovascular diseases; severe infection or inflammation) which is known to give an elevated measurement of ADM or of proADM partial peptide. For the control group, a mean value of 0.33±0.07 nmol/l (range from 0.10 to 0.64 nmol/l) of MR-proADM was determined. In an evaluation of the control persons according to age groups, a mean value of 0.337 nmol/l was obtained for the age group 38.3±13.9 years, and a mean value of 0.392 nmol/l for the selected age group 69.0±4,8 years (cf. FIG. 1).

Patients who had signs of dementia and who had been diagnosed with "probable Alzheimer's dementia" served as a patient group. A value of 0.614 nmol/l was obtained as a mean value for the patient group.

The measured MR-proADM concentrations in the plasma of healthy controls and patients with a probable Alzheimer's dementia are shown in FIG. 1.

The MR-proADM concentration is substantially increased in patients with a probable Alzheimer's dementia. Here, Alzheimer patients can be differentiated from healthy controls with a specificity of 95% (based on younger healthy controls with an age of 38.3±13.9) or of 82% (based on age-matched healthy controls with an age of 69.0±4.9) and a sensitivity of 89%.

Although increased ADM production, measured as MR-proADM concentration in plasma, is observed not only in the case of dementias but also in the case of other diseases (sepsis; cardiovascular diseases/heart failure; as a rule, however, these can be easily distinguished clinically from dementias) and MR-proADM is therefore not a brain-specific parameter, the MR-proADM determination, owing to the high specificity and sensitivity in AD patients is very suitable for purposes of supporting AD positive diagnosis and in particular for negative diagnosis (exclusion diagnosis), normal MR-proADM concentrations in the plasma of a patient suspected of suffering from AD can rule out with very high probability a diagnosis of AD.

Literature
1. BEINFELD M. C. (1998). Prohormone and pro-neuropeptide processing. Recent progress and future challenges. Endocrine 8:1-5
2. BELTOWSKI J., JAMROZ A. (2004). Adrenomedullin—what do we know 10 years since its discovery? Polish Journal of Pharmacology 56: 5-27
3. BUNTON D. C., PETRIE M. C., HILLIER C., JOHNSON F., MCMURRAY J. J. V. (2004). The clinical relevance of adrenomedullin: a promosing profile? Pharmacology & Therapeutics 103:179-201
4. CHU D. Q., SMITH D. M., BRAIN S. D. (2001). Studies of the microvascular effects of adrenomedullin and related peptides. Peptides 22:1881-1886
5. ELSASSER T. H., KAHL S., MARTINEZ A., MONTUENGA L. M., PIO R., CUTTITTA F. (1999). Adrenomedullin Binding Protein in the Plasma of Multiple Species: Characterization by Radioligand Blotting. Endocrinology 140(10): 4908-4911
6. ENDO T. (2001). A review of the biological properties and clinical implications of adrenomedullin and proadrenomedullin N-terminal 20 peptide (PAMP), hypotensive and vasodilating peptides. Peptides 22:1693-1711
7. FRANK R. A., GALASKO D., HAMPEL H., HARDY J., DE LEON M. J., MEHTA P. D., ROGERS J., SIEMERS E., TROJANOWSKI J. Q. (2003). Biological markers for therapeutic trials in Alzheimer's disease. Proceedings of the biological markers working group; NIA initiative on neuroimaging in Alzheimer's disease. Neurobiology of Aging 24: 521-536
8. GELDMACHER D. S. (2004). Dementia with Lewy bodies: diagnosis and clinical approach. Cleveland clinic Journal of Medicine 71:789-800
9. GROWDON J. H., SELKOE D. J., ROSES A., TROJANOWSKI J. Q., DAVIES P., APPEL S. et al. [Working Group Advisory Committee].(1998). Consensus report of the Working Group on Biological Markers of Alzheimer's Disease. [Ronald und Nancy Reagan Institute of the Alzheimer's Association and National Institute on Aging Working Group on Biological Biomarkers of Alzheimer's Disease]. Neurobiology of Aging 19: 109-116
10. ICHIKI Y., KITAMURA K., KANGAWA K., KAWAMOTO M., MATSUO H., ETO T. (1994). Distribution and characterization of immunoreactive adrenomedullin in human tissue and plasma. FEBS Letters 338:6-10
11. KIS B., ABRAHAM C. S., DELI M. A., KOBAYASHI H., WADA A., NIWA M., YAMASHITA H., UETA Y. (2001). Adrenomedullin in the cerebral circulation. Peptides 22:1825-1834
12. KITAMURA K., KANGAWA K., ISHIYAMA Y., WASHIMINE H., ICHIKI Y., KAWAMOTO M., MINAMINO N., MATSUO H., ETO T. (1994). Identification and hypotensive activity of proadrenomedullin N-terminal 20 peptide (PAMP). FEBS Letters 351(1): 35-37
13. KITAMURA K., KANGAWA K., ETO T. (2002). Adrenomedullin and PAMP: Discovery, Structures, and Cardiovascular Functions. Microsc. Res. Tech. 57:3-13.
14. MCKEITH I. G. (2002). Dementia with lewy bodies. British Journal of Psychiatry 180: 144-147
15. MEERAN K., O'SHEA D., UPTON P. D., SMALL C. J., GHATEI M. A., BYFIELD P. H., BLOOM S. R. (1997). Circulating adrenomedullin does not regulate systemic blood pressure but increases plasma prolactin after intravenous infusion in humans: a pharmacokinetic study. Journal of Clinical Endocrinology and Metabolism 82:95-100
16. MORGENTHALER N. G., STRUCK J., ALONSO C., BERGMANN A. (2005). Measurement of mid regional proadrenomedullin (MR-proADM) in plasma with an immunoluminometric assay. (Clinical Chemistry, 2005; in press)
17. M. GARY NICHOLLS, JOHN G. LAINBURY, LYNLEY K. LEWIS, DAVID O. MCGREGOR, A. MARK RICHARDS, RICHARD W. TROUGHTON, TIMOTHY G. YANDLE (2001). Bioactivity of adrenomedullin and proadrenomedullin N-terminal 20 peptide in man. Peptides 22 1745-1732.
18. SATOH F., TAKAHASHI K., MUR-AKAMI 0., TOTSUNE K., SONE M., OHNEDA M., ABE K., MIURA Y., HAYASHI Y., SASANO H. (1995). Adrenomedullin in human brain, adrenal glands and tumor tissues of pheochromocytoma, ganglioneuroblastoma and neuroblastoma. Journal of Clinical Endocrinology and Metabolism 80(5):1750-2

19. SELKOE D. J. (2001). Alzheimer's disease: genes, proteins, and therapy. Physiological Reviews 81: 741-766
20. STROUD R. M., WALTER P. (1999). Signal sequence recognition and protein targeting. Current Opinion Structure Biology 9:754-9
21. STRUCK J., CHEN T., MORGENTHALER N. G., BERGMANN A. (2004). Identification of an adrenomedullin precursor fragment in plasma of sepsis patients. Peptides 25: 1369-1372
22. SUGO S., MINAMINO N., KANGAWA K., MIYAMOTO K., KITAMURA K., SAKATA J., ETO T., MATSUO H. (1994). Endothelial cells actively synthesize and secrete adrenomedullin. Biochemical and Biophysical Research Communication 201(3): 1160-6
23. TARKOWSKI E. (2002). Cytokines in dementias. Current Drug Targets—Inflammation and Allergy 1: 193-200
24. TARKOWSKI E., LILJEROTH A. M., MINTHON L., TARKOWSKI A., WA1IN A., BLENNOW K. (2003). Cerebral pattern of pro- and anti-inflammatory cytokines in dementias. Brain Research Bulletin 61: 255-260
25. TAYLOR M. M., SAMSON W. K. (2001). Adrenomedullin and central cardiovascular regulation. Peptides 22:1803-1807
26. TEUNISSEN C. E., DE VENTE J., STEINBUSCH H. W. M., DE BRUIJN C. (2002). Biochemical markers related to Alzheimer's dementia in serum and cerebrospinal fluid. Neurobiology of Aging 23:485-508

The invention claimed is:

1. An in vitro method for the detection, for the determination of severity and for the monitoring and prognosis of neurodegenerative diseases, said method comprising determining the concentration of a physiologically inactive proadrenomedullin (proADM) partial peptide in a biological fluid of a patient who is suffering from a neurodegenerative disease or is suspected of suffering from such a disease, wherein a concentration of said proADM partial peptide that is elevated as compared to the concentration in healthy individuals is indicative of neurodegenerative disease in said patient.

2. The method according to claim 1, wherein the assay method is an immunodiagnostic assay method.

3. The method according to claim 1, wherein a midregional proadrenomedullin partial peptide (MR-proADM; SEQ ID NO: 2) which has the amino acids 45-92 of the complete preproadrenomedullin (SEQ ID NO: 1) is determined in the biological fluid of said patient.

4. The method of claim 2, wherein the immunodiagnostic assay method is an immunoassay of the sandwich type.

5. The method of claim 1, wherein the neurodegenerative disease is a presenile dementia selected from the group consisting of Alzheimer's dementia (AD), dementia with Lewy bodies (DLB), frontotemporal dementia (FTD) and various forms of vascular dementia (VAD).

6. The method according to claim 5, wherein said method is carried out as part of the diagnosis of Alzheimer's disease.

7. The method of claim 1, wherein said method is carried out as part of a multi-parameter determination in which at least one further biochemical or physiological parameter informative with regard to the respective clinical picture is simultaneously determined and in which a measured result is obtained in the form of a set of at least two measured variables, which is evaluated for the fine diagnosis of the neurodegenerative disease.

8. The method according to claim 7, wherein, as part of the multi-parameter determination, in addition to the determination of the proadrenomedullin partial peptide, at least one further biochemical parameter which is selected from the groups consisting of inflammation mediators, complement components, cytokines, chemokines, blood coagulants and fibrinolytic factors, acute-phase proteins and free radical compounds is determined.

9. The method according to claim 7, wherein the multi-parameter determination is effected as a simultaneous determination by means of a chip technology measuring apparatus or an immunochromatographic measuring apparatus.

10. The method of claim 7, wherein the evaluation of the complex measured result of the multi-parameter determination is effected with the aid of a computer program.

11. The method of claim 1, wherein said biological fluid is plasma.

12. The method of claim 1, wherein said concentration of proADM partial peptide in said biological sample is greater than 0.460 nmol/l.

* * * * *

SEQUENCE LISTING

```
<160> NUMBER OF SEQ ID NOS: 2

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Pro Ser Lys Ile Ser Pro Gln
    130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 48
<212> TYPE: PRT
<213> ORGANISM: Homo sapiens

<400> SEQUENCE: 2

Glu Leu Arg Met Ser Ser Ser Tyr Pro Thr Gly Leu Ala Asp Val Lys
1               5                   10                  15
```

```
-continued

Ala Gly Pro Ala Gln Thr Leu Ile Arg Pro Gln Asp Met Lys Gly Ala
20              25                  30

Ser Arg Ser Pro Glu Asp Ser Ser Pro Asp Ala Ala Arg Ile Arg Val
35                  40              45
```